US00PP19683P2

(12) United States Plant Patent
Lamb et al.

(10) Patent No.: US PP19,683 P2
(45) Date of Patent: Feb. 10, 2009

(54) ***ANTHURIUM* PLANT NAMED 'TWYANAL11'**

(50) Latin Name: *Anthurium hybrida*
Varietal Denomination: TWYANAL11

(75) Inventors: Ann E. Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,299

(22) Filed: Oct. 1, 2007

(51) Int. Cl.
*A01H 5/00* (2006.01)

(52) U.S. Cl. ..... Plt./368
(58) Field of Classification Search ..... Plt./367, Plt./368, 365
See application file for complete search history.

*Primary Examiner*—Annette H Para
*Assistant Examiner*—S. B McCormick Ewoldt
(74) *Attorney, Agent, or Firm*—Jondle & Associates, P.C.

(57) ABSTRACT

A new *Anthurium* plant particularly distinguished by having numerous, small lavender spathes, durable, abundant, shiny lanceolate leaves, a highly branched, spreading growth habit and being easy to grow, is disclosed.

1 Drawing Sheet

Genus and species: *Anthurium hybrida.*
Variety denomination: 'TWYANAL11'.

BACKGROUND OF THE NEW PLANT

The present invention comprises a new and distinct cultivar of *Anthurium,* botanically known as *Anthurium hybrida,* and hereinafter referred to by the cultivar name 'TWYANAL11'. The new cultivar originated from a hybridization made in 2003 in Apopka, Fla. USA. The female parent was the proprietary *Anthurium* plant 'T-263' (unpatented), while the male parent was the *Anthurium* plant 'Cotton Candy' (U.S. Plant Pat. No. 8,819).

The new cultivar was selected in April 2005 from the results of the hybridization and has been asexually reproduced repeatedly by tissue culture in Apopka, Fla., USA over a two and one-half year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla., 1) Numerous, small lavender spathes;
2) Durable, abundant, shiny lanceolate leaves;
3) Highly branched, spreading growth habit; and
4) Easy to grow.

DESCRIPTION OF PHOTOGRAPH

This new *Anthurium* plant is illustrated by the accompanying photograph which shows the overall plant habit including blooms, buds and foliage of the plant. The colors shown are as true as can be reasonably obtained by conventional photographic procedures. The photograph is of an 23-month old plant grown in a greenhouse in Apopka, Fla.

DESCRIPTION OF THE NEW CULTIVAR

The following detailed description sets forth the distinctive characteristics of 'TWYANAL11'. The data which define these characteristics were collected from asexual reproductions carried out in Apopka, Fla. The plant history was taken on 23-month old plants which were planted from tissue culture in 25-cm pots and grown in a greenhouse with average daily temperatures of 85° F.–95° F. and average nightly temperatures of 72° F. to 78° F. Observations were made in March 2007. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
- *Family.*—Aracea.
- *Botanical.*—*Anthurium hybrida.*
- *Common.*—*Anthurium.*

Parentage:
- *Female parent.*—'T-263', a proprietary *Anthurium* plant with dark-purple spathes (unpatented).
- *Male parent.*—*Anthurium* plant 'Cotton Candy' (U.S. Plant Pat. No. 8,819) with pink spathes.

Growth:
- *Form.*—Upright, symmetrical, with outward spreading leaves; plant wider than tall.
- *Growth and branching habit.*—Upright stems, highly branched (basal, axillary branching), dense leafy habit with many leaves and relatively small flowers; vigorous growth habit, plant produces numerous branches, leaves and flowers.
- *Height* (*measured from soil to top of canopy*).—30 cm to 38 cm.
- *Height* (*measured from soil to top of inflorescences*).—30 cm to 38 cm (flowers at, among and above the top of the foliage).
- *Width* (*area of spread*).—65 cm to 70 cm.

*Time to produce a finished flowering plant.*—Single micro cutting to liner: 14 to 16 weeks. 10 cm pot from liner: 6 to 7 months (first flowers). 15 cm pot from liner: 9 to 10 months. 20 cm pot from liner: 12 to 14 months.

*Growth rate.*—Typical of commercial *Anthurium* cultivars.

*Root description.*—Thick fleshy roots with finer laterals; between RHS 155D to RHS 174D (greenish-white) tinged with RHS 180D; between RHS 179A to RHS 179B where exposed to light; RHS 151D root tips.

*Durability of foliage to stresses.*—Durable, holds up well under typical commercial practice.

*High temperature tolerance.*—To about 104° F. without damage.

*Low temperature tolerance.*—To about 55° F. without damage.

Stems:

*Number of stems per plant.*—25.

*Length* (*from soil line to the junction of the last two unrolled leaves*).—7.5 cm.

*Diameter* (*measured from about* 3 *cm above the soil surface*).—1.2 cm.

*Internode length.*—1.1 cm.

*Color.*—Immature: Between RHS 145B to RHS 145C sheathed with green cataphylls. Mature: Between RHS 146C to RHS 146D sheathed with dried cataphylls between RHS 165A to RHS 165B (brown).

*Appearance.*—Upright, cylindrical, round, thick with regularly spaced petioles and short internodes; cataphylls are present and not persistant; surface is smooth and glossy.

*Aspect.*—Upright.

*Strength.*—Sturdy, strong, upright.

*Cataphylls.*—Shape and arrangement: Lanceolate, mucronate, acute, one or two keeled; base of cataphyll clasps the stem. Length: 3.7 cm to 11.0 cm. Width: 3.3 cm (flattened). Appearance: Inside: Shiny. Outside: Glossy. Pubescence: Absent (smooth). Color: Between RHS 144A to RHS 144B, becoming between RHS 165A to RHS 165B with senescence.

Leaves:

*Arrangement and type.*—Alternate, simple, single leaf per petiole; midrib on lower surface is keeled.

*Quantity of leaves per stem.*—10 per main stem; fewer leaves on younger axillary branches.

*Length.*—16 cm to 20 cm.

*Width* (*natural*).9.5 cm.

*Shape.*—Ovate to lanceolate.

*Apex.*—Acuminate, mucronate.

*Base.*—Acute.

*Margin.*—Smooth, entire, leaf blade and margin mostly flat.

*Appearance* (*on both surfaces*).—Smooth, thin, leathery, shiny; dulling with age.

*Pubescence* (*on both surfaces*).—Absent.

*Immature leaf color.*—Upper surface: Greener than, but closest to colors between RHS 146A to RHS 146B Lower surface; between RHS 146C to RHS 147C

*Mature leaf color.*—Upper surface: RHS 147A and tinged with RHS N189A. Lower surface: RHS 146B.

*Venation.*—Pinnate. Venation color: Upper surface: Immature: Between RHS 146B to RHS 146C. Immature midrib: RHS 146C. Mature: Same color as surrounding tissue. Mature midrib: RHS 146B. Lower surface: Immature: RHS 146C. Immature midrib: Between RHS 146D to RHS 145A. Mature: RHS 146C. Mature midrib: RHS 144B.

*Petiole.*—Aspect: Vertical, upright when newly emerged, leaning outward about 45° from the vertical axis with maturity. Length (from base of leaf to junction of petiole and stem): 21 cm to 25 cm. Diameter: Distal (measured in the center below the geniculum and above the petiole wing tip): 0.3 cm. Proximal: 0.8 cm. Color: Between RHS 146B to RHS 146C.

*Geniculum.*—Length: 3.1 cm. Diameter: 0.39 cm. Aspect: Straight or curved upward. Color: Between RHS 146B to RHS 146C.

*Wing.*—Length: 1.6 cm (tip of wing flush with petiole). Diameter: 0.5 cm. Color: Outside: Between RHS 146B to RHS 146C. Inside: RHS 146B.

Inflorescence:

*Arrangement.*—Spathe/spadix atop peduncle, emerges from petiole sheath; peduncle attached to stem at leaf axil; inflorescences among and slightly above the foliage, mostly along the margin of the leaf canopy; self-cleaning.

*Aspect.*—Upright straight, vertical when newly emerged, leaning outward toward the margin of the canopy with age.

*Height.*—30 cm to 38 cm,

*Depth.*—Spathe mostly flat or reflexed slightly along the margins.

*Flowering habit and season.*—Continuous flowering year round, but most prolific in winter and spring.

*Number of inflorescences per plant.*—22 inflorescences and buds.

*Buds.*—Are lanceolate, 3.9 cm to 5.7 cm long, 0.6 cm to 0.7 cm wide and are colored between RHS 62C to RHS 62B to RHS 73C while the proximal end is tinged with RHS 63B.

*Fragrance.*—Absent.

*Rate of inflorescence opening.*—About every 10 days, 3 to 4 new inflorescences emerge.

*Longevity on plant.*—3 to 4 weeks.

*Longevity as cut flower.*—10 days.

Spathe:

*Appearance.*—Relatively small, lavender; smooth, glossy, thin, leathery, margins slightly reflexed.

*Arrangement/Aspect.*—Variable; typically about 45° to 90° from the vertical axis.

*Pubescence* (*on both surfaces*).—Absent.

*Shape.*—Ovate.

*Margin.*—Entire; often slightly reflexed.

*Apex.*—Acute, mucronate.

*Base.*—Obtuse.

*Longevity.*—3 to 4 weeks with good color.

*Size.*—Length: 4.2 cm to 6.2 cm. Width (natural): 2.5 cm.

*Color.*—When opening: Front side: Between RHS 73B to RHS 68B. Rear side: Between RHS 62B to RHS 73B. Fully opened: Front side: RHS 63C. Rear side: RHS 63C. Fading to: Between RHS 65A to RHS 65B, becoming RHS N199B when senescent.

Spadix:

*Appearance.*—Columnar, upright, affixed atop very short stipe at junction of peduncle and spathe.

*Arrangement/Aspect.*—Upright, near vertical.

*Shape.*—Columnar, narrow, tapered at tip.

*Margin.*—Round in transverse section.

*Apex.*—Bluntly rounded, obtuse.

*Base.*—Bluntly rounded, terminates atop a short stipe.

*Size.*—Length: 3.3 cm to 4.0 cm. Diameter: 0.5 cm.

*Color* (*immature*).—Proximal: RHS 65D. Distal: Between RHS 70C to 70D.

*Color* (*mature*). Proximal: RHS 75B. Distal: RHS 75A.

Flowers:

*Arrangement.*—Individual flowers reduced, tightly packed on spadix.

*Type.*—Bisexual, reduced, minuscule; female flowers receptive first, followed by male flowers.

*Shape.*—Individual flowers roughly pyramidal in shape, tightly packed on the spadix; flowers sessile on spadix; face of individual flower flat and square or diamond shaped; pistil in center, protruding, surrounded by anthers; four triangular tepals at corners.

*Diameter.*—0.15 cm.

*Height.*—0.15 cm from base to tip of pistil; stigma protrudes about 0.005 cm when receptive.

*Number of female flowers per spadix.*—150.

*Number of male anthers per flower.*—About 8 (minuscule; not clearly visible).

Peduncle:

*Length.*—33 cm.

*Diameter.*—0.25 cm.

*Angle.*—Straight, upright or leaning outward toward the margin of the leaf canopy.

*Strength.*—Sturdy, somewhat flexible.

*Color.*—Between RHS 146C to RHS 144A.

Pedicel:

*Length* (*stipe*)—0.4 cm.

*Diameter* (*stipe*).—0.3 cm.

*Angle.*—Straight, upright.

*Strength.*—Sturdy.

*Color.*—RHS 146D.

Reproductive organs:

*Anther color.*—RHS 65D.

*Pollen amount.*—Sparse.

*Pollen color.*—RHS 155D (white).

*Stigma color.*—RHS 65D.

*Ovary color.*—RHS 65D.

Fruit and seed set: Seed production has not been observed to date

Disease and insect resistance: No particular resistance or susceptibility different from other *Anthurium* varieties.

COMPARISON WITH PARENTAL AND COMMERCIAL CULTIVARS

'TWYANAL11' differs from the female parent *Anthurium* plant 'T-263' (unpatented), by having numerous, small, light lavender spathes, while 'T-263' has fewer, larger dark-purple spathes. 'TWYANAL11' has leaves that are numerous and ovate to lanceolate in shape, while 'T-263' has fewer, larger, wider ovate leaves. In addition, 'TWYANAL11' has a highly branched, spreading growth habit, while 'T-263' has less branching and a more upright growth habit.

'TWYANAL11' differs from the male parent *Anthurium* plant 'Cotton Candy' (U.S. Plant Pat. No. 8,819) by having numerous, small, light lavender spathes, while 'Cotton Candy' has fewer, larger pink spathes. 'TWYANAL11' has leaves that are numerous and ovate to lanceolate in shape, while 'Cotton Candy' has fewer, larger, deltoid leaves. In addition, 'TWYANAL11' has a highly branched, spreading growth habit, while 'Cotton Candy' has less branching and a more rounded, clumping growth habit.

'TWYANAL11' differs from the commercial variety 'Purple Plum' (U.S. Plant Pat. No. 12,424), by having numerous, small, light lavender spathes, while 'Purple Plum' has fewer, larger purple spathes. 'TWYANAL11' has leaves that are numerous and ovate to lanceolate in shape, while 'Purple Plum' has fewer, broader, ovate leaves. In addition, 'TWYANAL11' has a highly branched, spreading growth habit, while 'Purple Plum' has less branching and a more upright growth habit.

I claim:

1. A new and distinct cultivar of *anthurium* plant as shown and described herein.

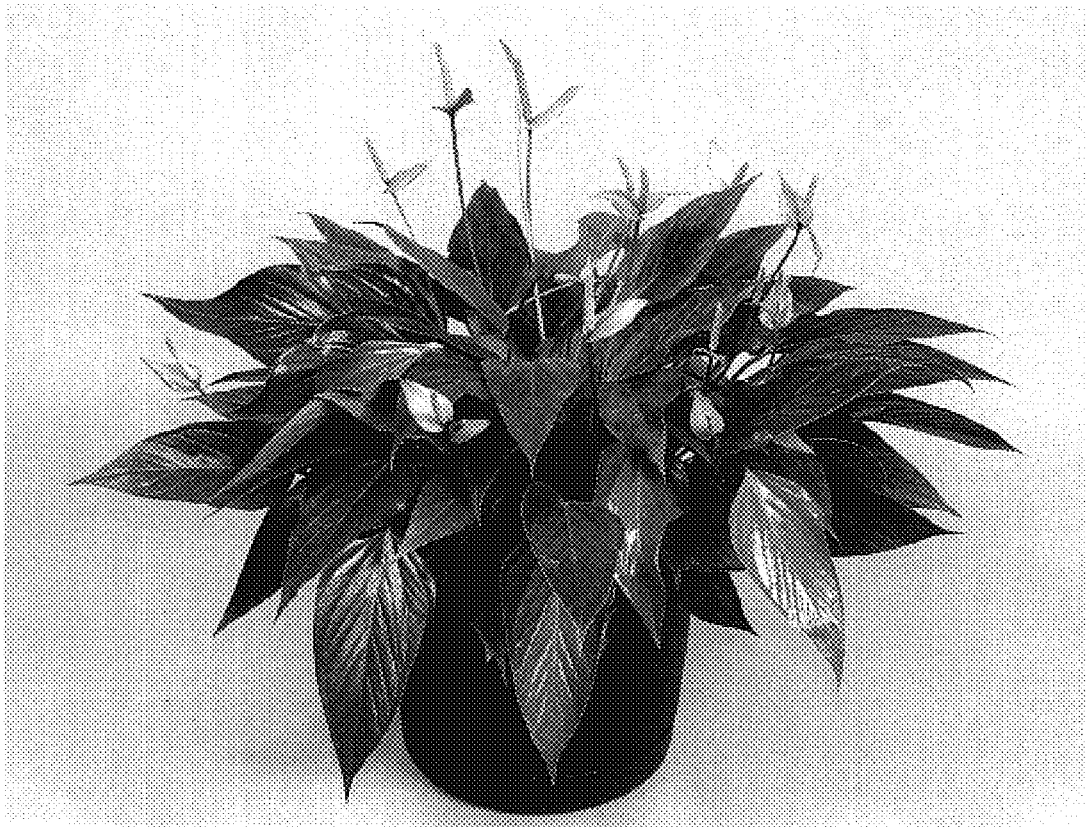

* * * * *